United States Patent [19]

Bundy

[11] 4,165,436
[45] Aug. 21, 1979

[54] TRANS-2,3-DIDEHYDRO-9-DEOXY-9-METHYLENE-PGF COMPOUNDS

[75] Inventor: Gordon L. Bundy, Portage, Mich.

[73] Assignee: The Upjohn Company, Kalamazoo, Mich.

[21] Appl. No.: 893,771

[22] Filed: Apr. 5, 1978

[51] Int. Cl.$^2$ .......................................... C07C 177/00
[52] U.S. Cl. ................................... 560/121; 260/408; 260/410.9 R; 260/413; 560/55; 568/838; 568/645; 568/646; 260/563 R; 260/570.5 CA
[58] Field of Search ............ 560/121; 260/408, 410.9, 260/413

[56] References Cited
U.S. PATENT DOCUMENTS
4,060,534  11/1977  Bundy ................................. 560/121

OTHER PUBLICATIONS
Derwent Abstract 79369Y/45 BE 854271 04-05-76.

Primary Examiner—Paul J. Killos
Attorney, Agent, or Firm—Robert A. Armitage

[57] ABSTRACT

The present specification relates to novel 9-deoxy-9-methylene-trans-2,3-didehydro-PGF compounds with improved pharmacological properties. While these compounds are useful in inducing a wide variety of prostaglandin-like pharmacological effects, they are specifically useful as regulators of procreation and fertility.

17 Claims, No Drawings

TRANS-2,3-DIDEHYDRO-9-DEOXY-9-METHYLENE-PGF COMPOUNDS

BACKGROUND OF THE INVENTION

The present invention particularly relates to novel 9-deoxy-9-methylene-trans-2,3-didehydro-PGF$_1$-type compounds and methods for their preparation and pharmacological use.

Trans-2,3-Didehydro prostaglandins are known in the art. See for example U.S. Pat. No. 3,931,296, incorporated herein by reference, which describes the preparation and pharmacological use of such compounds. Moreover, certain 9-deoxy-9-methylene-PGF-type compounds are likewise known in the art, and the preparation and use thereof is described in U.S. Pat. No. 4,060,534. The portion of the specification of the latter patent is likewise incorporated herein by reference for the purpose of describing the manner of preparation and pharmacological use for such compounds.

The naturally-occurring prostaglandins include compounds such as PGF$_2\alpha$ and PGE$_2$, depicted by Formulas I and II, respectively. These formulas, provided below, further indicate the carbon atom numbering for the natural prostaglandins.

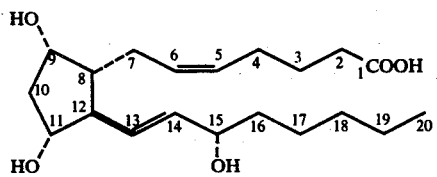

I

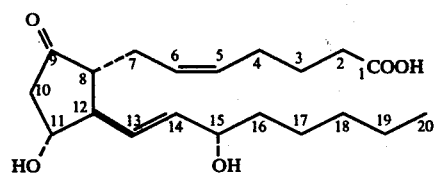

II trans-2,3-Didehydro-PGF$_1\alpha$ represents the positional isomer of PGF$_2\alpha$ wherein the 5,6-cis double bond is isomerized to a trans-2,3-double bond as indicated in Formula III.

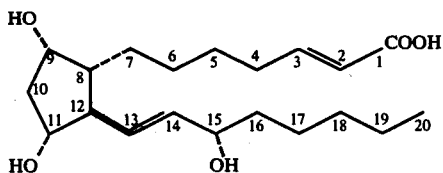

III

Formula IV provides the chemical structure for 9-deoxy-9-methylene-PGF$_2$, a compound wherein the C-9 hydroxyl of PGF$_2\alpha$ is replaced by a methylene.

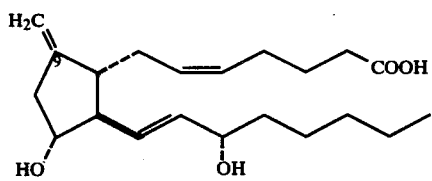

IV

The depiction of Formulas I–IV herein is the same as that described in U.S. Pat. No. 4,060,534. Moreover, Formulas III–IV depict "prostaglandin analogs", as that term is defined in U.S. Pat. No. 4,060,534. Finally, the various other conventions with respect to nomenclature and the like employed herein are the same as that described in U.S. Pat. No. 4,060,534.

SUMMARY OF THE INVENTION

The present invention particularly provides:
A prostaglandin of the formula

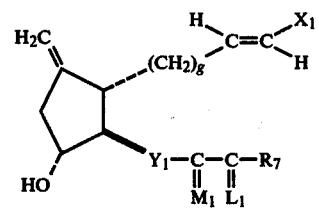

V where Y$_1$ is trans—CH=CH—, C≡C—, —CH$_2$CH$_2$—, or cis—CH=CH—;
wherein M$_1$ is

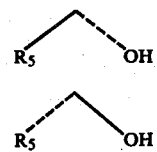

or

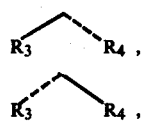

wherein R$_5$ is hydrogen or methyl;
wherein L$_1$ is

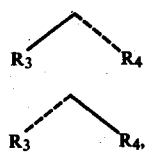

or a mixture of $R_3$  $R_4$ and $R_3$  $R_4$, wherein R$_3$ and R$_4$ are hydrogen, methyl, or fluoro, being the same or different, with the proviso that one of R$_3$ and R$_4$ is fluoro only when the other is hydrogen or fluoro;
wherein g is 4, 5, or 6;
wherein R$_7$ is
(1) —(CH$_2$)$_m$—CH$_3$.

(2)

, or

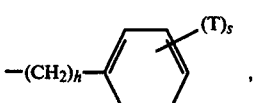

(3)

wherein h is zero, one, two, or three, wherein m is one to 5, inclusive, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

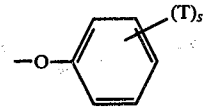

wherein T and s are as defined above, only when $R_3$ and $R_4$ are hydrogen or methyl, being the same or different; and wherein $X_1$ is (1) —COOR$_1$; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation.

(2) —CH$_2$OH, or (3) —CH$_2$NL$_2$L$_3$, wherein $L_2$ and $L_3$ are hydrogen, alkyl of one to 4 carbon atoms, inclusive or —COOR$_1$, wherein $R_1$ is as defined above; and the 1,11- or 1,15-lactones thereof when $X_1$ is —COOH.

The novel prostaglandin analogs described above are useful for the same purposes and in the same manner as the corresponding 9-deoxy-9-methylene-PGF-type compounds described in U.S. Pat. No. 4,060,534. However, in surprising and unexpected contrast to these prior art 9-deoxy-9-methylene-PGF-type compounds, the compounds of the present invention exhibit a substantially improved duration of activity, thus permitting the employment of smaller dosages or reducing the number of administrations required to obtain a desired pharmacological effect. Hence, these compounds are associated with fewer undesirable side effects than the corresponding 9-deoxy-9-methylene-PGF-type compounds previously known.

An especially important application of the compounds of the present invention reside in the regulation of procreation and fertility. Accordingly, these compounds are especially useful as regulators of the menstrual cycle, regulators of the estrous cycle, abortifacients, or labor inducers. When used for these purposes, U.S. Pat. No. 4,060,534 provides a general description of the manner of use; with the exception that, as indicated above, the novel prostaglandin analogs require somewhat smaller dosages or reduce the need for providing multiple administrations to a given patient or animal.

With regard to the novel prostaglandin analogs disclosed herein, certain compounds are preferred in that they exhibit increased potency and-or selectivity of action. Among the preferred prostaglandin analogs in accordance with the present invention are those wherein $Y_1$ is trans—CH═CH—. Further preferred are compounds wherein $R_3$ and $R_4$ are the same. Likewise, when $R_5$ is methyl, preferred compounds herein are those wherein $R_3$ and $R_4$ are both hydrogen. When at least one of $R_3$ and $R_4$ is not hydrogen, however, the preferred compounds herein are those wherein $R_5$ is hydrogen.

Compounds containing 7 and only 7 carbon atoms in the C-8 side chain are preferred. Thus, the preferred prostaglandin analogs herein are those wherein g is 4.

With respect to $R_7$, preferred compounds herein are those wherein m is 3 and h is zero or one. Likewise, s is preferably zero or one and T is preferable chloro, fluoro, or trifluoromethyl.

With regard to the carboxylic acids and esters, preferred compounds herein are those wherein $R_1$ is hydrogen, alkyl of one to 4 carbon atoms, inclusive, or a pharmacologically acceptable cation. Among the esters, further preferred compounds are those wherein $R_1$ is methyl or ethyl, most preferably being methyl.

Among the 2-decarboxy-2-aminomethyl-9-deoxy-9-methylene-trans-2,3-didehydro-PGF$_1$ compounds described herein, preferred compounds are those wherein $L_2$ and $L_3$ are both hydrogen. Further preferred in accordance with the present invention are the macrocyclic lactones, i.e., the 1,11- or 1,15-lactones when $X_1$ is —COOH.

Charts A and B describe the method by which the novel prostaglandin analogs herein are prepared. With respect to these charts, $Y_2$ is the same as $Y_1$, except that $Y_2$ is trans—CH═C(Hal)—, where Hal is chloro or bromo when $Y_1$ is —C≡C—.

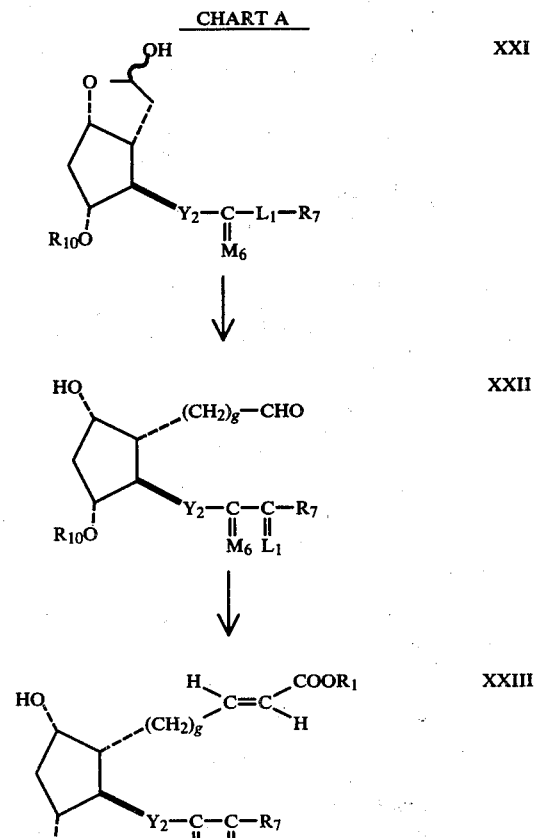

-continued

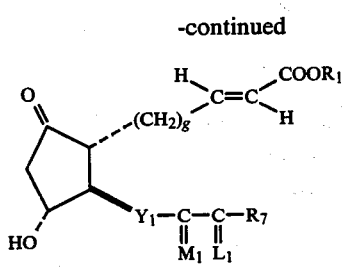

XXIV

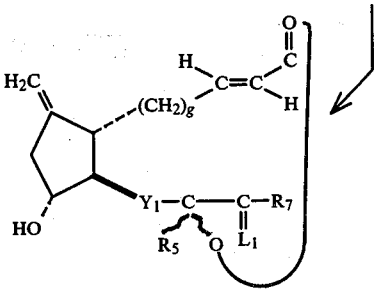

XXXV

CHART B

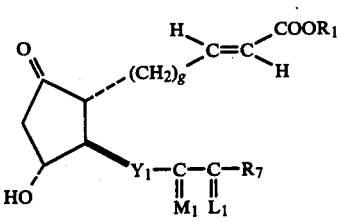

XXXI $R_{10}$ is a blocking group, preferably being an acetal-type blocking group such as tetrahydrofuran or tetrahydropyran, which is readily hydrolyzable under mild acetic conditions. Examples of appropriate blocking groups for use in the present charts is provided in U.S. Pat. No. 4,060,534. $M_6$ is the hydroxyl-derivatized form of $M_1$, wherein the hydroxyl is replaced by an ether linkage according to $R_{10}$.

With respect to Chart A, a method is provided wherein the Formula XXI compound is transformed to the Formula XXIV trans-2,3-didehydro-PGF$_1\alpha$-type precursor from which the novel prostaglandin analogs of this invention are prepared. The Formula XXI compound is known in the art, being the Formula XXXII compound of Chart A in U.S. Pat. No. 4,060,534.

The chemical steps employed in Chart A for the transformation of the Formula XXI compound to the corresponding trans-2,3-didehydro-PGE$_1\alpha$-type compound of Formula XXIV are likewise known in the art. In this regard, the transformation of the Formula XXI compound to the Formula XXII compound is accomplished by methods described in U.S. Pat. No. 3,931,296 (the Chart at columns 9–10). When g is 5 or 6, 3-carboxypropyl- or 4-carboxybutyltriphenylphosphonium bromide is employed in place of the 2-carboxyethyltriphenylphosphonium bromide reagent described on columns 9–10 of U.S. Pat. No. 3,931,296.

The Formula XXII compound is transformed to the Formula XXIII compound again by methods described in the chart on columns 9–10 of U.S. Pat. No. 3,931,296. Thereafter, the Formula XXIV compound is produced by dehydrohalogenation when $Y_2$ is trans—CH=C(-Hal), oxidation of the C-9— hydroxyl to a ketone, and finally hydrolysis of the $R_{10}$ blocking groups. Methods known in the art for such chemical conversions are employed. See particularly the methods described in U.S. Pat. No. 4,060,534.

Thereafter Chart B describes a method whereby the Formula XXXI compound is transformed to the various prostaglandin analogs of the present invention, i.e., the compounds of Formulas XXXII-XXXV.

The Formula XXXII compound of Chart B is prepared from the Formula XXXI compound by the method described in Chart D (columns 30–31) of U.S. Pat. No. 4,060,534.

Thereafter this novel 9-deoxy-9-methylene-trans-2,3-didehydro-PGF$_1$-type compound of Formula XXXII is transformed to its corresponding primary alcohol or primary amine by methods described in Chart F (column 31) or Chart G (columns 32–33), respectively, of U.S. Pat. No. 4,060,534. Alternatively, the Formula XXXII compound is transformed to the Formula XXXIV 1,11-lactone or Formula XXXV 1,15-lactone.

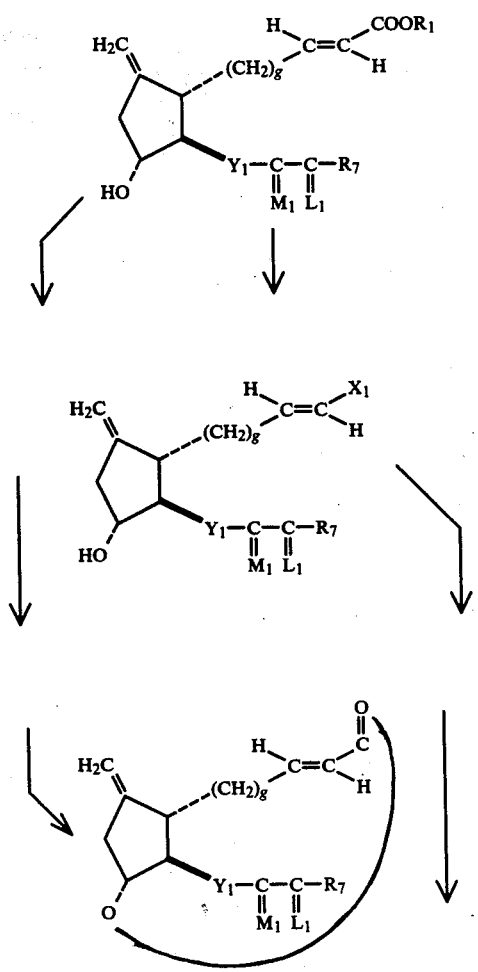

XXXII

XXXIII

XXXIV

Lactonization is accomplished by methods described in U.S. Pat. No. 4,032,543 or U.S. Pat. No. 4,045,449, respectively.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magentic Resonance) spectra are recorded on a Varian XL-100, A-60, A-60D, or T-60 spectrophotometer on deuterochloroform solutions with tetramethylsilane as an internal standard (downfield).

Mass spectra are recorded on a CEC model 21-110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine," herein, refers to an aqueous saturated sodium chloride solution.

The A-1X solvent system used in thin layer chromatography is made up from ethyl acetate-acetic acid-cyclohexane-water (90:20:50:100) as modified from M. Hamberg and B. Samuelsson, J. Biol Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone.

EXAMPLE 1 trans-2,3-Didehydro-9-deoxy-9-methylene-PGF$_1$, methyl ester (Formula V:

$X_1$ is —COOCH$_3$, g is 4, $Y_1$ is trans—CH═CH—, $R_3$ and $R_4$ of the $L_1$ moiety are both methyl, $R_5$ is hydrogen, and $R_7$ is n-butyl).

Refer to Chart B.

To a stirred solution S-methyl-S-phenyl-N-methyl-sulfoximine (1.39 g) in 20 ml of tetrahydrofuran under a nitrogen atmosphere cooled to 0°–5° C. is added methyl magnesium chloride (2.68 ml of a 2.9 M solution in tetrahydrofuran). After stirring for 20 min, the resulting mixture is cooled to −78° C. and added dropwise to a solution of 1.46 g of trans-2,3-didehydro-16,16-dimethyl-PGE$_1$, 11,15-bis(tetrahydropyranyl ether), methyl ester (prepared from 3α-tetrahydropyranyloxy-5-oxa-2β-(3α-tetrahydropyranyloxy-4,4-dimethyl-trans-1-octenyl)-1α-cyclopentane acid aldehyde γ-lactol according to the procedure of Reference Examples 2, 3, and 4 and Example 1 of U.S. Pat. No. 3,931,296) in 15 ml of tetrahydrofuran at −78° C. Thereafter the resulting mixture was stirred for 2.5 hrs and 2.5 ml of saturated ammonium chloride was added. After stirring for an additional 10 min the resulting mixture is then poured onto a mixture of ice, ammonium chloride, diethyl ether and extracted with diethyl ether. The ethereal extracts are then washed with brine, dried over sodium sulfate, filtered, and concentrated under reduced pressure to yield 2.55 g of an oil. This oil is then treated with aluminum amalgam according to the following procedure:

2 g of aluminum (30 mesh) are washed with diethyl ether, methanol, and added to 2.0 g of mercuric chloride in 75 ml of water. The resulting mixture is then shaken for about 30 sec until evolution of hydrogen gas becomes appreciable. Thereafter the solvent is decanted and the resulting amalgam washed successively with methanol and diethyl ether. This amalgam is then added to a solution of the oil obtained above in 65 ml of tetrahydrofuran, 10 ml of acetic acid, and 10 ml of water. The reaction mixture is then stirred at 15°–20° C. for 1 hr and thereafter diatomaceous earth (2 g) is added. The resulting mixture is then stirred for 5 min and filtered through a pad a diatomaceous earth. The solid residue is then washed with tetrahydrofuran and the combined filtrates concentrated under reduced pressure. The concentrate (contaminated with acetic acid and water) is then poured into 50 ml of brine and extracted with a 1:1 mixture of ethyl acetate and hexane. The organic phase is then washed with brine, disodium biphosphate, and dried over sodium sulfate. Removal of solvent under reduced pressure yields 1.86 g of an oil containing pure title product as bis(tetrahydropyranyl ether).

The crude tetrahydropyranyl ether (1.45 g) is treated with 75 ml of a 20:10:3 mixture of acetic acid, water, and tetrahydrofuran for 3 hr at 40° C. Removal of the solvents with benzene yields 1.46 g of crude title product. This crude material is chromatographed on 100 g of silica gel eluted with acetone and dichloromethane (1:4). Fractions containing pure title product are combined to yield 0.45 g. Silica gel TLC $R_f$ is 0.29 in acetone and dichloromethane (1:4). NMR absorptions are observed at 6.95, 5.92-5.65, 5.55, 4.85, 3.95-3.55, 3.69, 3.35-1.06, 0.90, 0.88, and 0.82 δ. Infrared absorptions are observed at 3450, 2995, 1750, 1660, 1430, 1270, 1195, 975, and 885 cm$^{-1}$. The mass spectrum for the trimethylsilyl derivative exhibits a demethylated high resolution peak at 521.3469, a molecular ion at 536 and other peaks at 505, 479, 437, 423, 415, 347, 323, and 243.

EXAMPLE 2

9-deoxy-9-methylene-trans-2,3-didehydro-PGF$_1$ (Formula V: $X_1$ is —COOH, g is 4, $Y_1$ is trans—CH═CH—, $R_3$ and $R_4$ of the $L_1$ moiety and $R_5$ of the $M_1$ moiety are all hydrogen, and $R_7$ is n-butyl).

By reaction with ethereal diazomethane trans-2,3-didehydro-PGE$_1$ (Example 2 of U.S. Pat. No. 3,931,296) is converted to trans-2,3-didehydro-PGE$_1$, methyl ester.

Following the procedure of Example 1, trans-2,3-didehydro-PGE$_1$, methyl ester is converted to trans-2,3-didehydro-9-deoxy-9-methylene-PGF$_1$, methyl ester.

Saponification of trans-2,3-didehydro-9-deoxy-9-methylene-PGF$_1$, methyl ester with sodium hydroxide according to the procedure of Example 4 of U.S. Pat. No. 4,060,534 yields the title product.

Further following the procedure of the above examples, there are prepared the various trans-2,3-didehydro-9-deoxy-9-methylene-PGF-type compounds of Formula XXXII in free acid or methyl ester form which exhibit the following side chain characteristics:
15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-trinor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-13,14-didehydro-;
16,16-Dimethyl-16-phenoxy-18,19,20-trinor-;
13,14-Didehydro-;
15-Methyl-13,14-didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,2+-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-fluorophenyl)-17,18,19,20-tetranor-13,14-didehydro-;
16-(p-fluorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenyl)-17,18,19,20-tetranor-13,14-didehydro-;
16-(p-fluorophenyl)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
15-Methyl-13,14-dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-didehydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
15-epi-13-cis-;
15-Methyl-15-epi-13-cis-;
16-Methyl-15-epi-13-cis-;
16,16-Dimethyl-15-epi-13-cis-;
16-Fluoro-15-epi-13-cis-;
16,16-Difluoro-15-epi-13-cis-;
17-Phenyl-18,19,20-trinor-15-epi-13-cis-;
17-(m-trifluoromethylphenyl)-18,19,20-trinor-15-epi-13-cis-;
17-(m-chlorophenyl)-18,19,20-trinor-15-epi-13-cis-;
17-(p-fluorophenyl)-18,19,20-trinor-15-epi-13-cis-;
16-Methyl-17-phenyl-18,19,20-trinor-15-epi-13-cis-;
16,16-Dimethyl-17-phenyl-18,19,20-trinor-15-epi-13-cis-;
16-Fluoro-17-phenyl-18,19,20-trinor-15-epi-13-cis-;
16,16-Difluoro-17-phenyl-18,19,20-trinor-15-epi-13-cis-;
16-Phenyl-17,18,19,20-tetranor-15-epi-13-cis-;
16-(m-trifluoromethylphenyl)-17,18,19,20-tetranor-15-epi-13-cis-;
16-(m-chlorophenyl)-17,18,19,20-tetranor-15-epi-13-cis-;
16-(p-fluorophenyl-17,18,19,20-tetranor-15-epi-13-cis-;
16-Phenyl-18,19,20-trinor-15-epi-13-cis-;

16-Methyl-16-phenyl-18,19,20-trinor-15-epi-13-cis-;
16-Phenoxy-17,18,19,20-tetranor-16-epi-13-cis-;
16-(m-trifluoromethylphenoxy-17,18,19,20-tetranor-15-epi-13-cis-;
16-(m-chlorophenoxy)-17,18,19,20-tetranor-15-epi-13-cis-;
16-(p-chlorophenoxy)-17,18,19,20-tetranor-15-epi-13-cis-;
16-Phenoxy-18,19,20-trinor-15-epi-13-cis-;
16-Methyl-16-phenoxy-18,19,20-trinor-15-epi-13-cis-;

EXAMPLE 3 trans-2,3-Didehydro-9-deoxy-9-methylene-PGF$_1$, 1,15- and 1,11-lactone

Following the procedure of Example 5 of U.S. Pat. No. 4,060,534, the title product of Example 2 is converted into the title product of the present example.

Further following the procedure of Example 3, there are prepared the various trans-2,3-didehydro-9-deoxy-9-methylene-PGF-type 1,11- or 1,15-lactones exhibiting the various side chain characteristics of those compounds described following Example 2.

EXAMPLE 4

2-Decarboxy-2-hydroxymethyl-trans-2,3-didehydro-9-deoxy-9-methylene-PGF$_1$.

Following the procedure of Example 6 of U.S. Pat. No. 4,060,534, the methyl ester corresponding to the title product of Example 2 is transformed to the title product of the present example.

Further following the procedure of Example 4, there are prepared the various 2-decarboxy-2-hydroxymethyl-trans-2,3-didehydro-9-deoxy-9-methylene-PGF-type compounds corresponding to each of the various methyl esters described following Example 2.

EXAMPLE 5

2-Decarboxy-2-aminomethyl-trans-2,3-didehydro-9-deoxy-9-methylene-PGF$_1$.

Following the procedure of Example 7 of U.S. Pat. No. 4,060,534, the methyl ester corresponding to the title product of Example 2 is transformed to the title product of the present example.

Further following the procedure of Example 4, there are prepared the various 2-decarboxy-2-aminomethyl-trans-2,3-didehydro-9-deoxy-9-methylene-PGF-type compounds corresponding to each of the various methyl esters described following Example 2.

I claim:

1. A prostaglandin analog of the formula

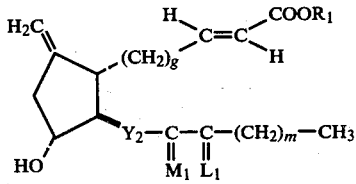

wherein m is one to 5, inclusive; wherein Y$_2$ is trans-CH=CH-, —CH$_2$CH$_2$—, or cis-CH=CH—; wherein M$_1$ is

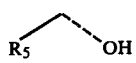

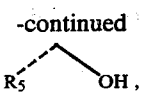

wherein R$_5$ is hydrogen or methyl; wherein L$_1$ is

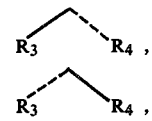

or a mixture of

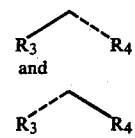

wherein R$_3$ and R$_4$ are hydrogen, methyl, or fluoro, being the same or different, with the proviso that one of R$_3$ and R$_4$ is fluoro only when the other is hydrogen or fluoro;
wherein g is 4, 5, or 6;
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation.

2. A prostaglandin analog according to claim 1, wherein m is 3.
3. A prostaglandin analog according to claim 2, wherein g is 4.
4. A prostaglandin analog according to claim 3, wherein Y$_2$ is —CH$_2$CH$_2$—.
5. trans-2,3-Didehydro-9-deoxy-9-methylene-13,14-dihydro-PGF$_1$, a prostaglandin analog according to claim 4.
6. A prostaglandin analog according to claim 3, wherein Y$_2$ is trans—CH=CH—.
7. A prostaglandin analog according to claim 6, wherein at least one of R$_3$ and R$_4$ is fluoro.
8. trans-2,3-Didehydro-9-deoxy-9-methylene-16,16-difluoro-PGF$_1$, a prostaglandin analog according to claim 7.
9. A prostaglandin analog according to claim 6, wherein at least one of R$_3$ and R$_4$ is methyl.
10. trans-2,3-Didehydro-9-deoxy-9-methylene-16,16-dimethyl-PGF$_1$, a prostaglandin analog according to claim 9.
11. trans-2,3-Didehydro-9-deoxy-9-methylene-16,16-dimethyl-PGF$_1$, methyl ester, a prostaglandin analog according to claim 9.
12. A prostaglandin analog according to claim 6, wherein R$_3$ and R$_4$ are both hydrogen.
13. A prostaglandin analog according to claim 12, wherein R$_5$ is methyl.
14. trans-2,3-Didehydro-9-deoxy-9-methylene-15-methyl-PGF$_1$, a prostaglandin analog according to claim 13.
15. A prostaglandin analog according to claim 14, wherein R$_5$ is hydrogen.
16. trans-2,3-Didehydro-9-deoxy-9-methylene-PGF$_1$, methyl ester, a prostaglandin analog according to claim 15.
17. trans-2,3-Didehydro-9-deoxy-9-methylene-PGF$_1$, a prostaglandin analog according to claim 15.

* * * * *